United States Patent
Duggal

(10) Patent No.: US 11,785,944 B2
(45) Date of Patent: Oct. 17, 2023

(54) PHENOLIC AEROSOL SPRAYS COMPRISING THYMOL

(71) Applicant: Vijay Duggal, Elmhurst, NY (US)

(72) Inventor: Vijay Duggal, Elmhurst, NY (US)

(73) Assignee: INNOTECT, New York City, NY (US)

( * ) Notice: Subject to any disclaimer, the term of this patent is extended or adjusted under 35 U.S.C. 154(b) by 0 days.

(21) Appl. No.: 17/006,830

(22) Filed: Aug. 29, 2020

(65) Prior Publication Data

US 2022/0061320 A1 Mar. 3, 2022

(51) Int. Cl.
*A01N 31/08* (2006.01)
*A01N 25/06* (2006.01)

(52) U.S. Cl.
CPC .............. *A01N 31/08* (2013.01); *A01N 25/06* (2013.01)

(58) Field of Classification Search
CPC ................................ A01N 31/08; A01N 25/06
USPC .......................................................... 424/49
See application file for complete search history.

(56) References Cited

U.S. PATENT DOCUMENTS

| | | | | |
|---|---|---|---|---|
| 3,632,782 A * | 1/1972 | Alburn | ................... | C07C 39/06 514/731 |
| 4,900,721 A * | 2/1990 | Bansemir | ............... | A01N 59/00 424/49 |
| 6,348,187 B1 * | 2/2002 | Pan | ......................... | A61K 8/22 424/49 |
| 6,641,799 B2 * | 11/2003 | Goldberg | ............. | A61K 9/0043 424/45 |
| 2005/0084454 A1 * | 4/2005 | Fust | ....................... | A61K 31/14 514/642 |
| 2006/0210842 A1 * | 9/2006 | Tezuka | .............. | H01M 8/04208 429/506 |
| 2008/0274163 A1 * | 11/2008 | Schwartz | ............. | A61K 9/0043 239/289 |

OTHER PUBLICATIONS

Google Search_Jul. 16, 2021_nasal spray essential oil hydrogen peroxide (Year: 2021).*

P.L. Cortelyou. "Use of Peroxide of Hydrogen in Diseases of the Throat and Nose," Transactions of the Medical Association of Georgia, Thirty-Ninth Annual Session, 1888, Macon, Georgia, 449-450. (Year: 1888).*

K. Xie, et al. Chronic toxicity of inhaled thymol in lungs and respiratory tracts in mouse model. Pharmacol Res Perspect. 2019; 1-10. (Year: 2019).*

A.A. Caruso, et al. "Might hydrogen peroxide reduce the hospitalization rate and complications of SARS-CoV-2 infection?", Infection Control & Hospital Epidemiology, 41: 1360-1361, published online by Cambridge University Press on Apr. 22, 2020. (Year: 2020).*

* cited by examiner

*Primary Examiner* — Frederick F Krass

(57) ABSTRACT

Disinfecting compositions for aerosols and vapors comprising thymol, monoterpenoids, essential oils and/or phenols wherein said compositions are fortified with antimicrobial agents of natural and/or synthetic origin. A method of disinfection of mucous membranes, skin, surfaces and air by using aerosols and vapors comprising thymol, monoterpenoids and/or phenols.

20 Claims, 1 Drawing Sheet

PHENOLIC AEROSOL SPRAYS COMPRISING THYMOL

TECHNICAL FIELD

The present invention generally relates to disinfecting compositions for aerosols comprising thymol, monoterpenoids and/or phenols. More specifically it relates to aerosol sprays or vapors comprising thymol that can be used for the treatment of mucous membranes and skin as well as for disinfection or surfaces and deodorization of air.

BACKGROUND OF THE INVENTION

Phenols and monoterpenoids comprising thymol are extremely versatile disinfectants however they need to used in a targeted manner preferably in the form of aerosol sprays for their effective use. Thymol can be combined with various other constituents disclosed herein to make it suitable for treatment and care of mucous membranes and skin as well as disinfection of surfaces and deodorization of air. Viruses often find their way into the respiratory system through mucous membranes of nasal cavities and throat which are hard to disinfect due to narrow passages lined with bodily fluids. This can lead to serious viruses such as COVID-19. Dispensing thymol in the form of nasal sprays, throat sprays and aerosol sprays for deodorization of air and surfaces can be very effective in inhibiting viruses.

"The lungs are the most common site of serious infection owing to their large surface area exposed to the external environment and minimum barrier defense. However, this architecture makes the lungs readily available for topical therapy. Therapeutic aerosols include those directed towards improving mucociliary clearance of pathogens, stimulation of innate resistance to microbial infection, cytokine stimulation of immune function and delivery of antibiotics. These therapeutics are still in their infancy, but show great promise."—US National Center for Biotechnology Information (NCBI): https://www.ncbi.nlm.nih.gov/pmc/articles/PMC4527977/

Thymol is known to kill listeria; it is commonly used as a constituent in many mouthwashes. The following prior art examples claim the use of thymol for oral care:

U.S. Pat. No. 5,723,106A by Warner Lambert Co LLC Reduced alcohol mouthwash antiseptic and antiseptic preparation. Claim:

1. An organoleptically acceptable antiseptic mouthwash composition comprising an effective amount of thymol, citral, eucalyptol, methyl salicylate and menthol dissolved in ethanol, said ethanol being present in an amount of no more than 22% v/v; a dispersion effective amount of surfactant; a co-solvent effective amount of a combination of propylene glycol and glycerin; benzoic acid; and water wherein the propylene glycol is present in an amount of from about 1.0% to about 4.0% v/v and said glycerin is present in an amount of from about 0.2% to about 3.0% v/v.

U.S. Pat. No. 4,945,087A by Warner Lambert Co LLC Taste masking of thymol. Claims:

1. A composition comprising thymol, an effective amount of a sugar alcohol, and an effective amount of anethole wherein the ratio of said sugar alcohol to said thymol is within the range of about 2750:1 to about 200:1, and the ratio of said anethole to said thymol is within the range of about 0.1:1 to about 1.75 to 1, wherein the combination of said sugar alcohol and said anethole mask the unpleasant taste of said thymol.

12. An oral hygiene composition comprising
(a) about 0.02 to about 0.1% by weight of thymol;
(b) about 20 to about 55% by weight of a sugar alcohol;
(c) about 0.01 to about 0.035% by weight of anethole;
(d) about 0.04 to about 0.12% by weight of citral, eucalyptol;
(e) about 0.02 to about 0.07% by weight of menthol;
(f) about 0.05 to about 0.25% by weight of benzoic acid;
(g) about 0.02 to about 0.09% by weight of methyl salicylate; and
(h) about 5 to about 35% by weight of ethanol;
wherein the unpleasant taste of said thymol is masked by said sugar alcohol and said anethole, and wherein said percents by weight are based on the total weight of the composition.

20. A method for masking the taste of thymol in a final product comprising adding an effective amount of a sugar alcohol and an effective amount of anethole to said product wherein the ratio of said sugar alcohol to said thymol is within the range of about 2750:1 to about 200:1, and the ratio of said anethole to said thymol is within the range of about 0.1:1 to about 1.75 to 1, wherein the combination of said sugar alcohol and said anethole mask the unpleasant taste of said thymol.

U.S. Pat. No. 6,689,342B1 by Johnson and Johnson Consumer Inc.:

"The present invention is related generally to oral care compositions, more particularly to oral care compositions comprising substituted tropolone compounds and essential oils, and methods of using the same for oral care." Claim:

1. An oral care composition comprising an oral care effective amount of:
a) a tropolone compound selected from the group consisting of methyl-7-hydroxymethyltropolone, 4-methyl-7-methoxymethyltropolone, 4,7-dimethyltropolone, 7-methyl-4-isopropyltropolone, 7-hiexyl-4-isopropyltropolone, 4-t-butyltropolone, 5-t-butyltropolone, 4-methyltropolorie, 7-methoxyrnethyl-4-isopropyltropolone, 7-hexloxymethyl-4-isopropyltropolone and combinations thereof;
b) at least one essential oil, and
c) a pharmaceutically acceptable oral carrier.

U.S. Ser. No. 08/784,609 by Warner Lambert Co LLC Reduced alcohol mouthwash antiseptic and antiseptic preparation. Claim:

1. An organoleptically acceptable antiseptic mouthwash composition comprising an effective amount of thymol, citral, eucalyptol, methyl salicylate and menthol dissolved in ethanol, said ethanol being present in an amount of no more than 22% v/v; a dispersion effective amount of surfactant; a co-solvent effective amount of a combination of propylene glycol and glycerin; benzoic acid; and water wherein the propylene glycol is present in an amount of from about 1.0% to about 4.0% v/v and said glycerin is present in an amount of from about 0.2% to about 3.0% v/v.

U.S. Pat. No. 7,867,509B2 by Johnson and Johnson Consumer Inc.
Fast dissolving orally consumable films. Claim:

1. A consumable film adapted to adhere to and dissolve in a mouth of a consumer, wherein said film comprises:
a. from about 40 to about 80 wt % of the film of a water soluble polymer, wherein the water soluble polymer is pullulan; and
b. an antimicrobial effective amount of an essential oil, wherein the essential oil comprises:
i. from about 0.01 to about 4 wt % of the film of thymol;
ii. from about 0.01 to about 4 wt % of the film of methyl salicylate;

iii. from about 0.01 to about 4 wt % of the film of citral, eucalyptol; and iv. from about 0.01 to about 15 wt % of the film of menthol.

Patent AU2003249466B2 by Warner Lambert Co LLC
Oral care composition comprising tropolone compounds and essential oils. Claim:

1. An oral care composition for preventing, eliminating or suppressing plaque, gum disease and oral malodor, comprising: (a) an oral care effective amount of a compound of Formula (I) 5 0 OH/\(b) an oral care effective amount of an essential oil mixture comprising thymol, citral, eucalyptol, menthol, and methyl salicylate; and 10 (c) an oral care effective amount of a pharmaceutically acceptable oral carrier comprising ethanol present in amounts of about 20% to about 30% by weight of said oral care composition, wherein the composition is effective at preventing, eliminating or suppressing plaque, gum disease and oral malodor.

10. An oral care composition for preventing, eliminating or suppressing plaque, gum disease and oral malodor, comprising: (a) an oral care effective amount of a compound of Formula (I) 0 OH/\15 (b) an oral care effective amount of an essential oil mixture comprising thymol, citral, eucalyptol, menthol, and methyl salicylate; and (c) an oral care effective amount of a pharmaceutically acceptable oral carrier 20 comprising ethanol present in amounts of about 20% to about 30% by weight of said oral care composition, wherein the composition is effective at preventing, eliminating or suppressing plaque, gum disease and oral malodour, substantially as hereinbefore described with reference to Example 1. Dated 20 Aug. 2009 25 Warner-Lambert Company LLC Patent Attorneys for the Applicant/Nominated Person SPRUSON & FERGUSON U.S. Pat. No. 9,132,103B2 by Conopco Inc.
Disinfecting agent comprising eugenol, terpineol and thymol
Claims:

1. A method of disinfecting a surface comprising the steps of
    (i) applying a composition comprising:
        (a) 0.005 to 5% by weight eugenol;
        (b) 0.01 to 5% by weight terpineol;
        (c) 0.01 to 5% by weight thymol; and
        (d) a carrier comprising water;
        on to a surface; and
    (ii) rinsing the surface with a suitable solvent or wiping the surface with a suitable wipe.

8. An antimicrobial composition comprising:
    a. 0.005 to 5% by weight eugenol;
    b. 0.01 to 5% by weight terpineol;
    c. 0.01 to 5% by weight thymol;
    d. 1 to 80% by weight of a surfactant; and
    e. a carrier comprising water
    wherein the composition is a personal wash, oral care or hard surface cleaning composition.

The aforementioned patents are claimed for oral care; none of these patents utilize thymol or phenols as aerosols or aerosol sprays. It is a big disadvantage because thymol is best utilized as an aerosol; it can be very effective even at low concentrations. In the form of sprays or aerosol sprays thymol can be targeted at mucous membranes or widespread in a space using aerosols or vapors. U.S. Pat. No. 9,132,103B2 by Conopco Inc. (Claim 1) advises to rinse off the composition after it has been applied over the surfaces; this would be wastage of the expensive constituents. Thymol is best utilized when it is left in place for long term effectiveness. Thymol is categorized by EPA as a pesticide; it can be harmful if used excessively. Thymol in low concentrations is effective as a mouthwash but it must be used sparingly. For treatment of nasal cavities, throat, gums and lesions within the mouth etc., targeted application of thymol is more effective than a mouthwash because unwanted exposure of thymol to surrounding tissues can be avoided. For example if one teeth hurts, a spray comprising thymol can be directed at that particular teeth without exposing the entire mouth to thymol by using a mouthwash. Similarly if there is throat infection the spray comprising thymol can be directed at throat without exposing other mucous membranes of the mouth. Spray application of thymol allows usage of thymol at higher concentrations targeting affected skin areas effectively while sparing surrounding tissues. Research shows that phenolic monoterpenes and monoterpenoids comprising thymol have wide range of applications for everyday care and treatment of mucous membranes and skin. Aerosols comprising thymol and phenols are very effective for disinfection of surfaces and deodorization of air; but the aforementioned prior arts fail to capture such potentials.

Additional information about this invention can be obtained by contacting the author by using the following URL: www.innotect.net/duggal or Twitter handle: @ArchitectDugg. All rights reserved by the author for the entire contents of this application.

BRIEF SUMMARY OF THE INVENTION

It is an object of the present invention to utilize phenols and thymol in a targeted manner in the form of sprays and aerosols to maximize its potential for disinfection of mucous membranes and skin as well as for disinfection of surfaces and deodorization of air. Natural phenols in the form monoterpenes and monoterpenoids comprising thymol are known for everyday care and disinfection of mucous membranes and skin as well as fore disinfection of surfaces and deodorization of air. Less expensive synthetic phenols may be substituted for disinfection of surfaces and air. The present invention discloses how thymol along with other constituents such as carvacrol, citral, eucalyptol, menthol, methyl salicylate anethole, eugenol, menthol, nootkatone, terpineol, limonene, borneol, terpinen-4-ol, camphor and phenol can be very effective for everyday care and medical treatment of mucous membranes and skin as well as for disinfection of surfaces and deodorization of air particularly when used as aerosol sprays. The aforementioned compositions can also be diffused or vaporized in the air by using a diffuser or vaporizer. The compositions disclosed herein can also be used as nasal wash, wound cleansing or other such skin care applications.

Many antiseptics are well known to kill germs on contact, however their long term exposure to internal bodily membranes poses risks. Thymol in this regard however is generally considered safe but is must be used sparingly. The present invention uses thymol and phenols in a targeted manner in the form of throat sprays, nasal sprays or skin sprays which can be manually operated to propel droplets or mist. Or the thymol compositions disclosed herein can be in the form of aerosols that can dispersed in the air by using a diffuser, or propelled from a sealed container to disinfect surfaces and air. Thymol at low concentrations such as 0.01% to 1% it can be effective for treatment and care of mucous membranes and gums. At 1% to 4% it can be effective for skin and scalp treatment. At 4% to 5% it can be effective for disinfecting surfaces and deodorizing air. The aforementioned percentages are given as examples only, they are not intended to limit the scope of the present invention. The present invention is equally applicable to domesticated animals some of whom are known to tolerate higher concentrations of thymol. The thymol aerosol sprays disclosed herein can also be used as pesticides, bug repellents and for mite control.

One embodiment of the present invention discloses composition 100 usable as an aerosol spray comprising thymol or a monoterpenoid phenol comprising thymol from 0.01% to 5% dissolved in ethanol; an effective amount of at least one essential oil comprising citral, eucalyptol, carvacrol, methyl salicylate, anethole, eugenol, menthol, nootkatone, terpineol, limonene, borneol, terpinen-4-ol, camphor or phenol; glycerin from 0.2% to about 20.0% v/v; a pharmaceutical grade carrier to maintain predetermined viscosity and an effective amount of surfactant. In different embodiments of the present invention composition 100 is fortified with additional constituents to make it suitable for different mucous membranes and skin as well as for disinfecting surfaces and deodorizing air.

To administer antiseptics to nasal cavities remains a challenge due to sensitive tissues and narrow structures lined with bodily fluids. It is an object of the present invention to use natural antiseptics such as thymol, carvacrol or monoterpenoid phenol(s) to disinfect mucous membranes as well as skin. The present invention uses thymol and/or carvacrol, as the key constituents for disinfection. In different embodiments of the present invention thymol is fortified with additional antibacterial agent(s) such as citral, eucalyptol, methyl salicylate, anethole, eugenol, menthol, nootkatone, p-cymene, terpineol, terpinen-4-ol or phenol to make the compositions suitable for nasal care, throat care, skin care, scalp care, ear edema care, teeth care, and gum care.

Thymol is a constituent of oil of thyme, a naturally occurring mixture of compounds in the plant *Thymus vulgaris* L. (or thyme). Thymol is available from other plants as well. Thymol is registered with the Environmental Protection Agency (EPA) and Food and Drug Administration (FDA) as a fungicide, medical disinfectant, and virucide which can be used to control pests including animal pathogenic bacteria and fungi, and several viruses including HIV-I. The present invention discloses various compositions in which thymol along with other constituents can be used for topical administration of mucous membranes and skin as well as well as through diffusion in the air such as aerosol sprays.

Thymol is a natural monoterpenoid phenol derivative of cymene ($C_{10}H_{14}O$) which is isomeric with carvacrol, found in oil of thyme, and extracted from *Thymus vulgaris*, ajwain and various other plants as a white crystalline substance of a pleasant aromatic odor and strong antiseptic properties.— (Wikipedia). Thymol is available from many plant sources such as *Monarda fistulosa* (wild bergamot, bee balm), *Monarda didyma* (crimson beebalm, scarlet beebalm, bergamot), *Origanum vulgare* (wild marjoram), *Origanum dictamnus* (cretan dittany, hop marjoram), *Trachyspermum ammi* (ajowan caraway and bishop's weed or carom). One embodiment of the present invention uses natural sources in the form of essential oils, plant extracts or thymol crystals in various compositions disclosed herein. These plant sources are comprised of several other beneficial chemicals such as carvacrol, terpinene, p-cymene and camphor. The compositions disclosed herein are based on laboratory grade thymol as well as thymol (thymol camphor) being part of an essential oil or plant extract which contain several other beneficial chemicals which are not specifically listed herein.

The present invention discloses disinfecting compositions for sprays, aerosols and vapors comprising thymol, monoterpenoids, essential oils and/or phenols wherein said compositions are fortified with antimicrobial agents of natural and/or synthetic origin. It also discloses a method of disinfection of mucous membranes, skin, surfaces and air by using aerosols and vapors comprising thymol, monoterpenoids, essential oils and/or phenols.

Thymol is synergist with several fortifying agents some of which are listed in tables A, B, 1 and 2 hereinafter. The present invention uses these fortifying agents such as phenols to further enhance the antimicrobial properties of compositions comprising thymol.

DETAILED DESCRIPTION OF THE INVENTION

The following are exemplary embodiments of the present invention; they are not meant to be restrictive. Claims should be referred to for the scope of the present invention. The terminology used herein is generic; terms from chemistry and organic chemistry are generally interchangeable. For example terms such as monoterpenoid and monoterpene are interchangeable in the context of the present invention. Monoterpenoid in chemistry is generally referred to as a terpenoid having a C10 skeleton while monoterpene in organic chemistry is generally referred to as a terpene formed from two isoprene units, and having ten carbon atoms, either hydrocarbons such as pinene, or compounds with functional groups such as camphor. One of the main constituent of the present invention is thymol (CAS number 89-83-8) with molecular formula $C_{10}H_{14}O$ regardless of its sources. The term aerosol spray in the context of the present invention generally applies to droplets or mist of the composition that can be propelled under pressure or diffused in the air. The droplets can be in the form of extremely fine mist (1-3 microns), ultra coarse (1000-2000 microns) or any other sizes in between. Some examples of droplet particle sizes are classified by classification system ASABE S-572.1. The compositions disclosed herein can also be diffused in the air by using a diffuser or vaporized by using a vaporizer. They can also be inhaled by using an inhaler. The present invention uses fortifying agents to further enhance the antimicrobial properties of thymol. The term fortifying agent herein refers to constituents that have antimicrobial properties which are additive or synergist with thymol. Some examples of fortifying agents are listed in tables A, B, 1 and 2 hereinafter.

Figure 1A:
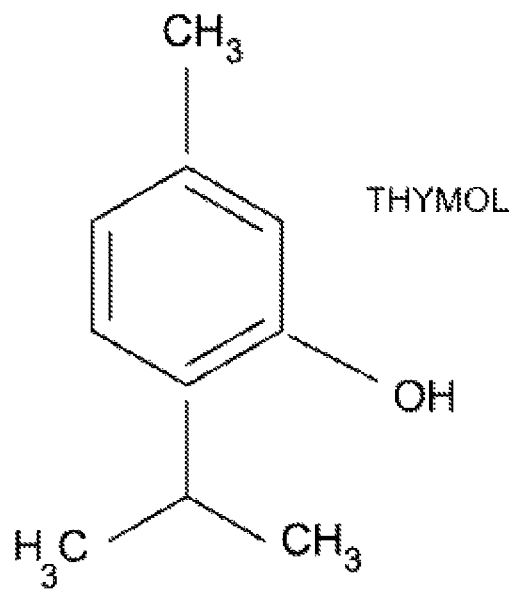
FIG. 1a: Schematic showing chemical structure of thymol
Figure 1B:
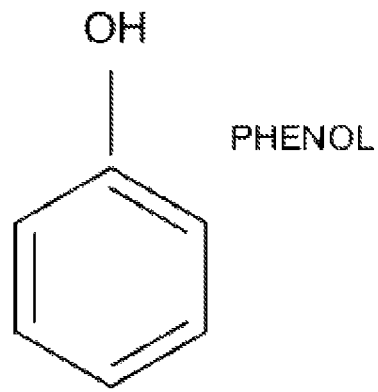
FIG. 1b: Schematic showing chemical structure of phenol
Figure 1C:
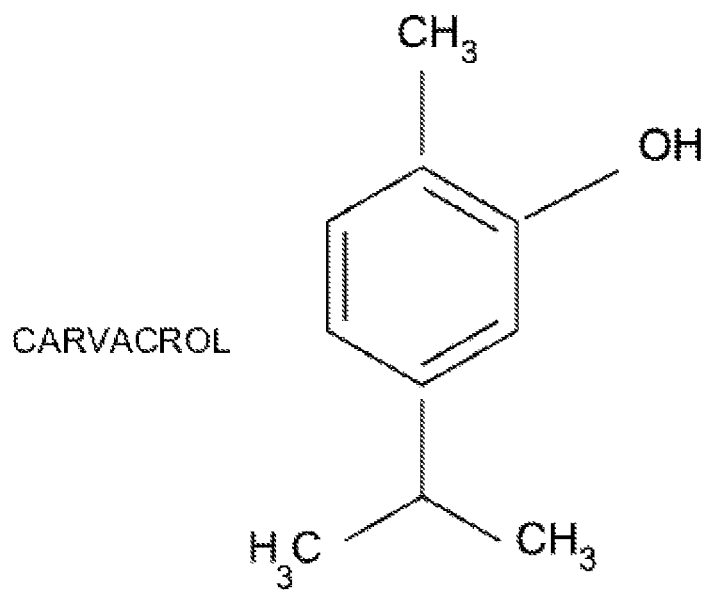
FIG. 1c: Schematic showing chemical structure of carvacrol

FIGS. 1a, 1b and 1c show chemical structures of thymol, phenol and carvacrol which are the key constituents of the disinfecting aerosol compositions disclosed herein.

The present invention discloses disinfecting composition 100 comprising thymol or a monoterpenoid comprising thymol from 0.01% to 5% dissolved in ethanol; an effective amount of at least one constituent from the following group: Citral, eucalyptol, carvacrol, methyl salicylate, anethole, eugenol, menthol, terpineol, limonene, borneol, terpinen-4-ol, camphor or phenol; glycerin from 0.2% to about 20.0% v/v; a pharmaceutical grade carrier to maintain predetermined viscosity, and an effective amount of surfactant wherein composition 100 is usable as an aerosol spray.

Composition 100 may also include an effective amount of skin conditioner, an effective amount of preservative, and a pH adjuster.

Thymol used for composition 100 can be part of an essential oil or plant extract having substantial amounts of thymol (which may also contain carvacrol); or it can be laboratory grade thymol. In different embodiments of the invention composition 100 is fortified with other constituents to make it suitable for different mucous membranes of the body and skin as well as for disinfection of surfaces and air. Some of these constituents are listed in tables A, B, 1 and 2 hereinafter.

The National Center for Biotechnology Information (NCBI), US National Institutes of Health (NIH) describes the uses of thymol and carvacrol as follows: "Thymol and carvacrol from the class of monoterpene phenols are one of the most potent plant essential oil components possessing antimicrobial effects. Known for their wide bioactive spectrum, these positional isomers of isopropyl cresol deplete ergosterol content, compromise membrane permeability, block efflux pumps and restore antifungal susceptibility to fluconazole in resistant *Candida* strains. Exposure to these natural compounds induces a cascade of stress responses, which are important to comprehend their microbicidal mechanisms." More detailed information and other uses of thymol can be found at the following web sources:
https://pubmed.ncbi.nlm.nih.gov/25681060/
https://www.ncbi.nlm.nih.gov/pmc/articles/PMC3418667/
https://www.ncbi.nlm.nih.gov/pmc/articles/PMC6105452/
https://www.ncbi.nlm.nih.gov/pmc/articles/PMC4872997/
https://www.ncbi.nlm.nih.gov/pmc/articles/PMC4040322/
https://www.ncbi.nlm.nih.gov/pmc/articles/PMC7185619/
Additional information about monoterpene phenols can be also be found at:
https://chempedia.info/info/monoterpenic_phenol/

Thymol is listed in the EPA registry as: Phenol, 5-methyl-2-(1-methylethyl)—CAS number 89-83-8 with molecular formula $C_{10}H_{14}O$. Carvacrol is identified with CAS number 499-75-2. The compositions disclosed herein can be formed by using laboratory grade thymol or by using essential oils or plant extracts that contain substantial amounts of thymol. These plant sources may also contain other chemicals such as carvacrol, terpinene, p-cymene and camphor. Many commercially available essential oils of thyme, oregano or ajwain (ajwain flower crystals, *Trachyspermum ammi*) are rich in thymol and also contain carvacrol. These plants contain several other beneficial chemicals which are not specifically mentioned herein but are part of the present invention when monoterpene or monoterpenoid phenols are specified. Some of these chemicals are identified by Yoshiaki Noma and Yoshinori Asakawa in their publication Comprehensive Natural Products II which is also briefly described at:
https://www.sciencedirect.com/topics/medicine-and-dentistry/thymol.

Thymol (also known as 2-isopropyl-5-methylphenol, IPMP) is a natural monoterpene (monoterpenoid) phenol derivative of cymene, $C_{10}H_{14}O$, isomeric with carvacrol, found in oil of thyme, and extracted from *Thymus vulgaris* (common thyme, Spanish thyme or other such varieties), ajwain and various other kinds of plants as a white crystalline substance of a pleasant aromatic odor and strong antiseptic properties. Thymol also provides the distinctive, strong flavor of the culinary herb thyme, also produced from *T. vulgaris*.—Wikipedia Thymol is sometimes part of other chemicals and is referred to by other names such as: Methyl phenol, 5-methyl-2-(1-methylethyl)-; p-Cymen-3-ol; Thyme camphor; 2-Isopropyl-5-methylphenol; 3-Hydroxy-p-cymene; 3-Methyl-6-isopropylphenol; 5-Methyl-2-isopropylphenol; 6-Isopropyl-m-cresol; 6-Isopropyl-3-methylphenol; m-Cresol, 6-isopropyl-; p-Cymene, 3-hydroxy-; Phenol, 2-isopropyl-5-methyl-; Thymic acid; 1-Hydroxy-5-methyl-2-isopropylbenzene; 1-Methyl-3-hydroxy-4-isopropylbenzene; 3-p-Cymenol; 3-Hydroxy-1-methyl-4-isopropylbenzene; 5-Methyl-2-isopropyl-1-phenol; 5-Methyl-2-(1-methylethyl)phenol; Isopropyl-m-cresol; m-Thymol; 2-Hydroxy-1-isopropyl-4-methylbenzene; NSC 11215; 2-Isopropyl-5-methylphenol (thymol); Isopropyl cresol. The aforementioned constituents are part of the present invention where thymol is specified herein.

Thymol or thyme oil is known to be beneficial for prevention of skin irritation, wound healing, bronchitis, whooping cough, sore throat, parasitic worm infections, tonsillitis, bad breath and skin disorders. It is used as a germ-killer in mouthwashes and liniments. It is also applied to the scalp to treat baldness and to the ears to fight bacterial and fungal infections. It can also be used with another chemical such as chlorhexidine as gum disinfectant dental varnish to prevent tooth decay. Thyme contains chemicals that might help bacterial and fungal infections, skin irritation and wound care. It also might relieve smooth muscle spasms, such as coughing, and have antioxidant effects. The present invention utilizes thymol in a targeted manner in the form of aerosols sprays to maximize its effectiveness while addressing the aforementioned conditions.

Natural phenols comprising thymol are specialized varieties of essential oil constituents that feature an alcohol group attached to an aromatic benzene ring. An aromatic benzene ring is a six-carbon ring structure with three double bonds. The electrons in this ring system are arranged in such a way that they are "shared" between all of the carbon atoms, giving benzene the unique characteristic of acting like it has an electron excess and resulting in its unique properties. This structure contributes to the powerful antioxidant properties of phenols as well as many other beneficial properties. Phenol constituents are very potent, which may cause irritation to the skin. Oils with high phenol content should be diluted before topical application. Many natural phenols are found in essential oils that also contain thymol and carvacrol. In different embodiments of the present invention composition 100 is fortified with natural phenols, synthetic phenols, and essential oils containing as eugenol, antheole and camphor. The following tables from Wikipedia list some of the natural and synthetic phenols that are part of the present invention:

TABLE A

| Naturally occurring Phenols | |
| --- | --- |
| Cannabinoids | the active constituents of cannabis |
| Capsaicin | the pungent compound of chili peppers |
| Carvacrol | found in, i.a., oregano; antimicrobial and neuroprotectant |
| Cresol | found in coal tar and creosote |
| Estradiol | estrogen- hormones |
| Eugenol | the main constituent of the essential oil of clove |
| Gallic acid | found in galls |
| Guaiacol | (2-methoxyphenol) - has a smokey flavor, and is found in roasted coffee, whisky, and smoke |

TABLE A-continued

Naturally occurring Phenols

| | |
|---|---|
| Methyl salicylate | the major constituent of the essential oil of wintergreen |
| Raspberry ketone | a compound with an intense raspberry smell |
| Salicylic acid | precursor compound to Aspirin (chemical synthesis is used in manufacturing) |
| Serotonin/dopamine/ adrenaline/noradrenaline | natural neurotransmitters |
| Thymol | (2-Isopropyl-5-methyl phenol) - found in thyme; an antiseptic that is used in mouthwashes |
| Tyrosine | an amino acid |
| Sesamol | a naturally occurring compound found in sesame seeds |

TABLE B

Synthetic Phenols

| | |
|---|---|
| Phenol | the parent compound, used as a disinfectant and for chemical synthesis |
| Bisphenol A | and other bisphenols produced from ketones and phenol/cresol |
| BHT | (butylated hydroxytoluene) - a fat-soluble antioxidant and food additive |
| 4-Nonylphenol | a breakdown product of detergents and nonoxynol-9 |
| Orthophenyl phenol | a fungicide used for waxing citrus fruits |
| Picric acid | (trinitrophenol) - an explosive material |
| Phenolphthalein | pH indicator |
| Xylenol | used in antiseptics & disinfectants |

Carvacrol, thymol and eugenol belong to a class of naturally presenting phenols with a ten-carbon unit, which are present in essential oils of many plants. They are wide ranging of biological and pharmaceutical activities such as anti-inflammatory, antimicrobial, analgesic, anticancer and antioxidant. The present invention uses aforementioned constituents in the compositions disclosed herein. Additional information of their uses can be found at The National Center for Biotechnology Information (NCBI), US National Institutes of Health web site at: https://pubmed.ncbi.nlm-.nih.gov/28988386/. Laboratory grade thymol or monoterpene/monoterpenoid phenols containing thymol have wide range of uses for skin care, scalp care, throat care, ear care, nasal care, gum care and teeth care. The present invention uses thymol as one of the active ingredient in composition 100 disclosed herein. In different embodiments of the present invention composition 100 is fortified with other constituents to make it suitable for medical care of different mucous membranes and skin as well as for disinfection of surfaces and air. The following are some of the examples:

In one embodiment of the invention composition 100 is fortified with an effective amount of chlorhexidine, chlorhexidine gluconate, chlorhexidine acetate or sodium fluoride for dental care, oral care and skin care.

In one embodiment of the invention composition 100 is fortified with citric acid, ascorbic acid, carbolic acid, maleic acid, aspartic acid, gluconic acid, succinic acid, glucuronic acid, sodium glutamate, fumaric acid, carboxylic acid, zinc chloride, citrate, and/or benzoic acid to make it suitable for mucus membrane and skin care.

In one embodiment of the invention composition 100 is fortified with an effective amount of betadine, centramide or chloroxylenol to make it suitable for skin treatment.

In one embodiment of the invention composition 100 is fortified with an effective amount of skin conditioner such as hyaluronic Acid, vitamin B5, vitamin E, panthenol, aloe vera gel or aloe vera leaf extract to make it suitable for skin care.

In one embodiment of the invention composition 100 is fortified with an effective amount of pharmaceutical grade an quaternary ammonium compound such as cetylpyridinium chloride (CPC) or domiphen bromide to make it suitable for oral care.

In one embodiment of the invention composition 100 is fortified with an effective amount of pharmaceutical grade fluticasone to make it suitable for nasal care and treatment.

In one embodiment of the invention composition 100 is fortified with an effective amount of pharmaceutical grade cyclodextrin such as methylated beta-cyclodextrin (MβCD) to enhance its antibacterial properties.

In one embodiment of the invention composition 100 is fortified with an effective amount of pharmaceutical grade hydrogen peroxide to enhance its antibacterial properties.

In one embodiment of the invention composition 100 is fortified with an effective amount of pharmaceutical grade polyhexanide (polyhexamethylene biguanide, PHMB) to make it suitable for mucus membrane and skin treatment.

In one embodiment of the invention composition 100 is fortified with an effective amount of nootkatone to make it suitable for bug repellent spray.

In one embodiment of the invention composition 100 is fortified with an effective amount of pharmaceutical grade streptomycin to enhance its antimicrobial properties.

In one embodiment of the invention composition 100 is fortified with an effective amount of phenol to make it suitable for disinfection of surfaces and air.

In one embodiment of the invention composition 100 is fortified with an effective amount of N-alkyl ethylbenzyl dimethyl ammonium (c12-c14) to make it suitable for disinfection of surfaces and air.

In one embodiment of the invention composition 100 is fortified with an effective amount of at least one pharmaceutical grade antiseptic constituents from table A hereinbefore.

In one embodiment of the invention composition 100 is fortified with an effective amount of at least one pharmaceutical grade antiseptic constituents from table B hereinbefore.

In one embodiment of the invention composition 100 is fortified with an effective amount of at least one pharmaceutical grade antiseptic constituents from table 1 hereinafter.

In one embodiment of the invention composition 100 is fortified with an effective amount of at least one pharmaceutical grade antiseptic constituents from table 2 hereinafter.

Tables 1 and 2 hereinafter contains a list of antiseptic agents as published by the National Institute of Health, United States. It should be noted that presently many of these constituents are not approved for the treatment of mucous membranes. Clinical trials must be conducted, and approval sought from governmental authorities before their use; the same is applicable to other constituents listed in the present application.

In one embodiment of the invention the compositions disclosed herein are used as nasal wash and skin treatment applications.

In one embodiment of the invention the compositions disclosed herein are used as sprays, aerosol sprays, aerosols or vapors.

TABLE 1

| Active ingredient | Patient antiseptic skin preparation | Health care personnel hand wash | Health care personnel hand rub | Surgical hand scrub | Surgical hand rub |
|---|---|---|---|---|---|
| Alcohol 60 to 95 percent | 2 Y | 3 N | Y | N | Y |
| Benzalkonium chloride | Y | Y | Y | Y | N |
| Benzethonium chloride | Y | Y | N | Y | N |
| Chlorhexidine gluconate | N | N | N | N | N |
| Chloroxylenol | Y | Y | N | Y | N |
| Cloflucarban | Y | Y | N | Y | N |
| Fluorosalan | Y | Y | N | Y | N |
| Hexylresorcinol | Y | Y | N | Y | N |
| Iodine complex (ammonium ether sulfate and polyoxyethylene sorbitan monolaurate) | N | Y | N | Y | N |
| Iodine complex (phosphate ester of alkylaryloxy polyethylene glycol | Y | Y | N | Y | N |
| Iodine tincture United States Pharmacopeia (USP) | Y | N | N | N | N |
| Iodine topical solution USP | Y | N | N | N | N |
| Nonylphenoxypoly (ethyleneoxy) ethanoliodine | Y | Y | N | Y | N |
| Poloxamer-iodine complex | Y | Y | N | Y | N |
| Povidone-iodine 5 to 10 percent | Y | Y | N | Y | N |
| Undecoylium chloride iodine complex | Y | Y | N | Y | N |
| Isopropyl alcohol 70-91.3 percent | Y | N | Y | N | Y |
| Mercufenol chloride | Y | N | N | N | N |
| Methylbenzethonium chloride | Y | Y | N | Y | N |
| Phenol (equal to or less than 1.5 percent) | Y | Y | N | Y | N |
| Phenol (greater than 1.5 percent) | Y | Y | N | Y | N |
| Secondary amyltricresols | Y | Y | N | Y | N |
| Sodium oxychlorosene | Y | Y | N | Y | N |
| Triclocarban | Y | Y | N | Y | N |
| Triclosan | Y | Y | N | Y | N |
| Combinations: | | | | | |
| Calomel, oxyquinoline benzoate, triethanolamine, and phenol derivative | Y | N | N | N | N |
| Mercufenol chloride and secondary amyltricresols in 50 percent alcohol | Y | N | N | N | N |
| Triple dye | Y | N | N | N | N |

1 Hexachlorophene and tribromsalan are not included in this table because they are the subject of final regulatory action (see section IV.D.3).
2 Y = Eligible for specified use.
3 N = Ineligible for specified use.
Source: https://www.federalregister.gov/documents/2017/12/20/2017-27417/safety-and-effectiveness-of-health-care-antiseptics-topical-antimicrobial-drug-products-for#print

TABLE 2

Chemical composition of various essential oils and their antibacterial activity against human pathogens:

| MAPs | Part used | Major chemical compounds |
|---|---|---|
| *Achillea clavennae* | Leaves and flowers | Camphor, myrcene, 1,8-cineole, β-caryophyllene, linalool, geranyl acetate |
| *Achillea fragrantissima* | Aerial parts | Yomogi alcohol, 1,8-cineole, artemisia alcohol, thujone |
| *Achillea ligustica* | Aerial parts | Viridiflorol, terpinen-4-ol |
| *Artemisia absinthium* | Aerial parts | Myrcene, trans-thujone, trans-sabinyl acetate |
| *Artemisia biennis* | Aerial parts | (Z)-Beta-ocimene, (E)-beta-farnesene, acetylenes, (Z)- and (E)-En-yn-dicycloethers |
| *Artemisia cana* | Aerial parts | Santolina triene, alpha-pinene, camphene |
| *Artemisia dracunculus* | Aerial parts | Methylchavicol, methyl eugenol, beta-phellandrene, terpinolene |
| *Artemisia longifolia* | Aerial parts | Alpha-pinene, camphene, 1,8-cineole |

TABLE 2-continued

Chemical composition of various essential oils and their antibacterial activity against human pathogens:

| MAPs | Part used | Major chemical compounds |
|---|---|---|
| *Artemisia frigida* | Aerial parts | 1,8-Cineole, methylchavicol, camphor |
| *Cinnamomum zeylancium* | Bark, leaves | Cinnamaldehyde |
| *Copaifera officinalis* | Essential oil | β-Caryophyllene, β-bisabolene, germacrene B, α-copaene, germacrene D, α-humulene, δ-cadinene |
| *Coriandrum sativum* | Leaves | 2E-Decenal, decanal, 2E-decen-1-ol, n-decanol |
| *Cuminum cyminum* | Leaves | γ-Terpin-7-al, γ-terpinene, β-pinene, cuminaldehyde |
| *Cymbopogon citratus* | Fruit | Ethanolic compounds |
| *Cymbopogon nardus* | Leaves, stems | Δ2-Carene, beta-citronellal |
| *Cyperus longus* | Arial part | β-Himachalene, α-humulene, γ-himachalene |
| *Daucus littoralis* | Leaves, stems, roots, flowers, fruits | Germacrene D, acorenone B |
| *Dracocephalum foetidum* | Leaves | n-Mentha-1,8-dien-10-al, limonene, geranial, neral |
| *Eremanthus erythropapps* | Leaves | (Z)-Caryophyllene, germacrene D, viridiflorol, p-cymene, γ-terpinene |
| *Eugenia caryophyllata* | Flower buds | Phenylpropanoids such as carvacrol, thymol, eugenol, cinnamaldehyde |
| *Euphrasia rostkoviana* | Essential oil | n-Hexadecanoic acid, thymol, myristic acid, linalool |
| *Foeniculum vulgare* | Leaves | Trans-anethole, methylchavicol, limonene |
| *Fortunella margarita* | Leaves | Gurjunene, eudesmol, muurolene |
| *Juniperus phoenicea* | Arial part | α-Pinene, β-phellandrene, α-terpinyl acetate |
| *Laurus nobilis* | Arial part | citral, eucalyptol (1,8-cineole), linalool |
| *Lavandula × intermedia* "Provence" (Blue Lavandin) (a cross between *L. angustifolia*, *L. Latifolia*) | Arial part | Camphor, citral, eucalyptol (1,8-cineole), linalool, β-pinene, α-pinene |
| *Juniperus excelsa* | Leaves and twigs | α-Pinene, α-cedrol, δ-car-3-ene |
| *Lippia sidoides* | Leaves | Thymol and carvacrol |
| *Mentha piperita* | Arial part | |
| *Mentha pulegium* | Arial part | Piperitone, piperitenone, α-terpineol, pulegone |
| *Mentha suaveolens* | Arial part | Pulegone, piperitone, cis-cis-p-menthenolide, limonene germacrene |
| *Melaleuca alternifolia* (tea tree oil) | Essential oil | Terpinen-4-ol, 1,8-cineole, γ-terpinene, α-terpinene, terpinolene |
| *Momordica charantia* | Seed | Trans-nerolidol, apiole, cis-dihydrocarve, ol germacrene D |
| *Myrtus communis* | Leaves | Eugenol, α-terpineol, γ-terpinene |
| *Nigella sativa* | Seeds | Thymoquinone, p-cymene, α-thujene, thymohydroquinone, longifolene |
| *Ocimum gratissimum* | Leaves | Eugenol, methyl eugenol, cis-ocimene, trans-ocimene, α-pinene, camphor |
| *Ocimum kilimandscharicum* | Flowers and leaves | Eugenol, borneol, linalool, methyl eugenol |
| *Origanum vulgare* | Leaves, Arial part | Carvacrol, thymol, γ-terpinene, trans-sabinene hydrate, cis-piperitol, borneol, terpinen-4-ol, linalool |
| Ocimum basilicum | Leaves, stems | γ-Terpinene, methylchavicol |
| *Petroselinum sativum* | Leaves, stems | Myristicin, apiol, 1,2,3,4-tetramethoxy-5-(2-propenyl)-benzene |
| *Piper nigrum* | Essential oil | Limonene, δ-3-carene, α-pinene, β-caryophyllene, β-pinene, sabinene, α-felandeno, myrcene, para-cymene, linalool, terpinolene, β-selinene, 1,8 cineole, α-terpinene, α-humulene, α-copaene, eugenol, terpinen-4-ol, camphene, safrole |
| *Pimpinella anisum* | Seed | Trans-anethole |
| *Plectranthus barbatus* | Leaves | (Z)-Caryophyllene, germacrene D, viridiflorol, p-cymene, γ-terpinene |
| *P. amboinicus* | Leaves | (Z)-Caryophyllene, germacrene D, viridiflorol, p-cymene, γ-terpinene |
| *Plectranthus neochilus* | Leaves | α-Pinene, β-pinene, trans-caryophyllene, caryophyllene oxide |
| *Pogostemon cablin* | Leaves | Patchoulol, δ-guaieno; gurjunene-α, α-guaiene, aromadendrene, β-patchoulene |

TABLE 2-continued

Chemical composition of various essential oils and their antibacterial activity against human pathogens:

| MAPs | Part used | Major chemical compounds |
|---|---|---|
| *Rosmarinus officinalis* | Leaves, flower | Camphor, camphene, limonene, geraniol, myrcene, linalool benzoylacetate, linalool, α-pinene, α-terpinolene, bornyl acetate, borneol |
| *Satureja hortensis* | Arial part | Carvacrol, thymol, γ-terpinene |
| *Salvia sclarea* | Arial part | Linalool, linalyl acetate, geranyl acetate, β- ocimene acetate, caryophyllene oxide |
| *Salvia officinalis* | Arial part | α-Thujone, camphor, 1,8-cineole, α-pinene |
| *Salvia lavandulifolia* | Essential oil | Camphor, α-thujone, beta-thujone, camphene, α-pinene, terpineol |
| *Satureja cuneifolia* | Aerial parts | Carvacrol and p-cymene |
| *Struchium sparganophora* | Leaves | β-Caryophyllene, germacrene A, α-humulene, germacrene D |
| *Syzygium aromaticum* | Leaves, flower bud | Eugenol, eugenylacetate |
| *Syzygium cumini* | Leaves | α-Pinene, β-pinene, trans- caryophyllene, 1,3,6-octatriene, delta-3-carene, α-caryophyllene, α-limonene |
| *Trachyspermum ammi* | Seeds | — |
| *Thymus zygis* | Essential oil | — |
| *Thymus mastichina* | Leaves, stems | m-Thymol, carvacrol, trans-caryophyllene |
| *Thymus kotschyanus* | Arial part | Carvacrol, 1,8 cineole, thymol, borneol, E-caryophyllene |
| *Thuja* sp. (*Thuja plicata, Thuja occidentalis*) | Essential oil | Alpha-thujone and beta-thujone |
| *Verbena officinalis* | Arial part | Borneol, geranoil |
| *Warionia saharae* | Arial part | β-Eudesmol, trans-nerolidol, linalool, 1,8 cineole, camphor, p-cymene, terpinen-4-ol |

Sources: https://www.ncbi.nlm.nih.gov/pmc/articles/PMC5206475/ and https://www.ncbi.nlm.nih.gov/pmc/articles/PMC5206475/table/tab1/?report=objectonly In one embodiment of the present invention the disinfecting compositions disclosed herein are fortified with at lease one quaternary ammonium compound. Quaternary ammonium compounds (commonly known as quats or QACs) are cationic surfactants (surface active agents) that combine bactericidal and virucidal (generally only enveloped viruses) activity with good detergency and, therefore, cleaning ability. Although other surfactant types, such as anionic, nonionic and, amphoteric surfactants (referring to their overall charge) have some antimicrobial activity depending on the specific biocide, the cationic surfactants (and some of the amphoterics) have the greatest antimicrobial activity. Examples include hexadecyltrimethylammonium ('cetrimide'), chlorhexidine, and benzalkonium chloride."—C. P. Chauret, Encyclopedia of Food Microbiology: https://www.sciencedirect.com/topics/neuroscience/quaternary-ammonium-compounds#:~:text=Third %20Edition)%2C %202009-,Quaternary %20Ammonium %20Compounds, and %2C %20therefore %2C %20cleaning %20ability. The surfactants used for the compositions disclosed herein can be nonionic, anionic, cationic or amphoteric.

More information about thymol, carvacrol and phenolic monoterpenoids can be obtained from a publication titled "Structural Requirements for Monoterpenoid Activity against Insects" by Pamela J. Rice and Joel R. Coats of Iowa State University: https://pubs.acs.org/doi/pdf/10.1021/bk-1994-0557.ch008. The utilization of the present invention is free for medical personnel and first responders for their personal use provided no money is made in its manufacturing and distribution. The aerosolized compositions disclosed herein must be used under the guidance or a doctor. The author and assignee of the present application do not assume any legal liability for their use; governmental approvals must be sought before their use.

The web references provided herein are for convenience only; they are not part of this specification. If these online references change or become unavailable overtime this would not affect the specification and principles of the present invention as these descriptions and principles are described in the summary and detailed description of the present invention.

The embodiments of the present invention as described herein are for examples only; they should not be used in a limiting sense to interpret the scope of the present invention. Different embodiments of the present invention can be combined to developed other embodiments. Any embodiments developed by extrapolation or combination of the claims are within the scope of the present invention.

The invention claimed is:

1. A nasal spray, comprising a fine mist spray comprising aerosolized droplets <100 microns in sizes produced by a nasal spray device from a liquid composition, comprising one or more monoterpenoids(s) from about 0.01%-1%; hydrogen peroxide from about 1% to 3%; glycerin from about 0.2% to 20%; and water.

2. The nasal spray of claim 1 wherein said fine mist spray further comprises an effective amount of a solvent or surfactant.

3. The nasal spray of claim 1 wherein said fine mist spray further comprises ethanol from 0.5%-40%.

4. The nasal spray of claim 1 wherein said fine mist spray further comprises an effective amount of chlorhexidine gluconate.

5. The nasal spray of claim 1 wherein said fine mist spray further comprises an effective amount of cetylpyridinium chloride.

6. The nasal spray of claim 1 wherein said fine mist spray further comprises an effective amount of benzalkonium chloride.

7. The nasal spray of claim 1 wherein said fine mist spray further comprises an effective amount of a pharmaceutically acceptable carrier.

8. The nasal spray of claim 1 wherein said fine mist spray further comprises an effective amount of a pharmaceutically acceptable preservative.

9. The nasal spray of claim 1 wherein said fine mist spray further comprises an effective amount of hyaluronic acid, vitamin B5, tocopheryl acetate, panthenol, lactic acid, aloe vera gel or aloe vera leaf extract.

10. A nasal spray, or a mucous membrane spray, consisting essentially of a fine mist spray consisting essentially of aerosolized droplets <100 microns in sizes produced by a spray device from a liquid composition, consisting essentially of thymol, carvacrol or a combination thereof from about 0.01%-1%; ethanol from 0.5%-40%; hydrogen peroxide from about 1% to 3%; glycerin from about 0.2% to 20%; and water.

11. The nasal spray or mucous membrane spray of claim 10 wherein said fine mist spray further consists essentially of an effective amount of hyaluronic acid, vitamin B5, tocopheryl acetate, panthenol, lactic acid, aloe vera gel or aloe vera leaf extract.

12. The nasal spray or mucous membrane spray of claim 10 wherein said fine mist spray further consists essentially of an effective amount of a surfactant.

13. The nasal spray or mucous membrane spray of claim 10 wherein said fine mist spray further consists essentially of an effective amount of chlorhexidine gluconate.

14. The nasal spray or mucous membrane spray of claim 10 wherein said fine mist spray further consists essentially of an effective amount of cetylpyridinium chloride.

15. The nasal spray or mucous membrane spray of claim 10 wherein said fine mist spray further consists essentially of an effective amount of benzalkonium chloride.

16. The nasal spray or mucous membrane spray of claim 10 wherein said fine mist spray further consists essentially of an effective amount of a pharmaceutically acceptable carrier.

17. The nasal spray or mucous membrane spray of claim 10 wherein said fine mist spray further consists essentially of an effective amount of a pharmaceutically acceptable preservative.

18. The nasal spray or mucous membrane spray of claim 10 wherein said fine mist spray further consists essentially of an effective amount of eugenol, citral, eucalyptol, methyl salicylate, anethole, menthol, nootkatone, terpineol, terpinen-4-ol, limonene, borneol, geraniol or camphor.

19. A nasal spray, consisting essentially of a fine mist spray consisting essentially of aerosolized droplets <100 microns in sizes produced by a nasal spray device from a liquid composition, consisting essentially of one or more monoterpenoid(s) from about 0.01%-1%; hydrogen peroxide from about 1% to 3%; glycerin from about 0.2% to 20%; and water.

20. The nasal spray of claim 19 wherein said fine mist spray further consists essentially of an effective amount of a solvent, surfactant, chlorhexidine gluconate, cetylpyridinium chloride, or benzalkonium chloride.

* * * * *